A United States Patent [19]
Field et al.

[11] 4,283,393
[45] Aug. 11, 1981

[54] TOPICAL APPLICATION OF INTERFERON INDUCERS

[75] Inventors: Arthur K. Field, North Wales; Richard J. Harwood, Philadelphia, both of Pa.

[73] Assignee: Merck & Co., Inc., Rahway, N.J.

[21] Appl. No.: 20,125

[22] Filed: Mar. 13, 1979

[51] Int. Cl.³ .............................................. A61K 31/70
[52] U.S. Cl. ..................................... 424/180; 424/85; 536/28; 536/29
[58] Field of Search ...................... 536/28, 29; 424/85, 424/180

[56] References Cited

U.S. PATENT DOCUMENTS

| | | | |
|---|---|---|---|
| 3,734,097 | 5/1973 | Zaffaroni | 424/22 |
| 3,821,193 | 6/1974 | Fare et al. | 536/28 |
| 3,845,201 | 10/1974 | Haddad et al. | 424/180 |
| 4,124,702 | 11/1978 | Lapson et al. | 536/28 |

OTHER PUBLICATIONS

Field et al., "Proc. Nat. Ac. Sci.", vol. 58, No. 3, pp. 1004-1010, Sep. 1967.
Kaufmann et al., "Am. Jour. Ophthal.", vol. 68, No. 3, pp. 486-491, Sep. 1969.
Nesburn et al., "Am. Jour. Ophthal.", vol. 72, No. 4, pp. 821-826, Oct. 1971.

*Primary Examiner*—Johnnie R. Brown
*Attorney, Agent, or Firm*—Edmunde D. Riedl; Mario A. Monaco

[57] ABSTRACT

Virus infections of eye, skin and mucous membrane tissue are effectively treated by controlled release topical application of interferon inducers.

8 Claims, No Drawings

TOPICAL APPLICATION OF INTERFERON INDUCERS

BACKGROUND OF THE INVENTION

This invention is concerned with the prevention and treatment of virus infections of eye, skin and mucous membrane tissue by the controlled release topical application of interferon inducers.

Interferon is a class of soluble proteins that inhibit virus multiplication. They are produced by cells in response to a virus infection and are not virus-specific in their inhibitory actions.

The cellular production of interferon also can be induced by certain materials other than viruses such as double-standard synthetic polynucleotide complexes (dsRNA) as reported by Field et al., *Proc. Nat. Ac. Sci.*, 58, 1004–1010 (1967), and U.S. Pat. No. 4,124,702, especially polyriboinosinic acid:polyribocytidylic acid. This material is otherwise known as poly I:poly C, poly I:C, poly rI:poly rC, or $rI_n.rC_n$ and is hereinafter referred to as poly I:C.

Furthermore, dsRNA such as poly I:C have been successfully used to induce resistance against systemic as well as localized infections. Topical application of drugs, including interferon inducers, often require frequent repeated treatments in order to insure adequate drug exposure of the infected tissue. This limitation has been a serious problem, especially for potential application of antiviral drugs to mucous membranes and the cornea and conjunctiva of the eye.

Surprisingly, it has now been found that controlled release topical application of interferon inducers is very effective in the local topical treatment of virus infections of the eye, skin and mucous membrane tissue.

It is therefore an object of this invention to provide a method of treating virus infections of the eye, skin and mucous membrane tissue by topical application of an interferon inducer by a controlled release means whereby there is provided an optimum amount of interferon inducer at the site of the infection for a prolonged period of time.

It is a further object of this invention to provide controlled release formulations comprising an interferon inducer, particularly for use in the treatment of virus infections of the eye, skin and mucous membrane tissue.

DETAILED DESCRIPTION OF THE INVENTION

The novel method of treatment of this invention comprises the topical application of an interferon inducer by a controlled release means to virus infected eye, skin or mucous membrane tissue. By this method a substantially optimum therapeutic amount of interferon inducer is applied to the virus infected tissue over a prolonged period of time and is thereby made an effective method of treating such virus infections.

Interferon inducers useful in the novel method of treatment of this invention are double-stranded synthetic polynucleotide complexes such as poly I:C, poly A:U or the like; natural double-stranded RNA derived from virus infected bacterial cells, such as MU9-dsRNA or dsRNA isolated from Penicillium species, and non-polynucleotide inducers such as Tilorone hydrochloride, 1,3-dimethyl-4-(3-dimethylamino-propylamino)-1H-pyrazolo-[3,4,-b]-quinoline dihydrochloride or the like.

A novel means for accomplishing the controlled release of an interferon inducer is to incorporate, in a homogeneous manner, the interferon inducer into a matrix consisting of a water-soluble polymer which is solid at or near body temperature. The water-soluble polymer is a cellulose ether such as methylcellulose, hydroxyethylcellulose, hydroxy-propylcellulose, hydroxypropylmethylcellulose, or sodium carboxymethylcellulose, or other pharmaceutically acceptable polymer such as polyvinyl alcohol, polyvinylpyrrolidone, carboxyvinylpolymer, polyethylene glycol or the like. The preferred water-soluble polymer is hydroxypropylcellulose. Amounts of about 0.0025 to about 0.4 mg of interferon inducer per 1 mg of formulation is appropriate, preferably about 0.075 to about 0.25 mg of interferon inducer per 1 mg of formulation.

For treatment of virus infections of the skin, such as by the Herpes group of viruses, it is convenient to employ the novel formulation of this invention in the form of a sheet with a thickness of about 0.25 to about 3.0 mm, preferably about 1 mm with an area approximating the area to be treated and held in place by bandaging materials.

An alternate means of accomplishing the novel controlled release application of this invention on the skin is by use of a specially designed bandage for the purpose, such as disclosed in U.S. Pat. Nos. 3,734,097 and 3,797,494, and U.S. Application Ser. No. 960,354, filed Nov. 13, 1978 by Harwood.

For treatment of virus infections of the eye, rectangular or rod shaped pieces of the formulation of about 2.5–12 mg may be inserted between the eye and the lower eyelid.

For use as vaginal inserts or rectal suppositories, the controlled release formulations of this invention are in the usual sizes and shapes and contain between about 2.5–250 mg of interferon inducer per 1 g of formulation.

The following Examples describe two experiments comparing the beneficial effect of the novel method of treatment of this invention in the eye, with certain control treatments, and a typical ophthalmic insert formulation.

From the results it is concluded that rabbit eye treatment using poly I:C insert was effective in preventing or substantially delaying and reducing the Herpes virus infection, as measured by reduction of virus production. This protective effect was the result of effective controlled delivery of the interferon inducer, poly I:C. Treatment of animals with either placebo inserts or poly I:C in PBS did not effectively alter virus infection.

EXAMPLE 1

New Zealand white rabbits were infected with Herpes simplex virus Type 1 (HSV-1) by dropping 0.05 ml containing approximately 10 infectious doses onto the cornea of each eye. Animals were treated (2 animals per group, four eyes total) with:

(1) 200 $\mu$g of poly I:C in 0.1 ml of phosphate buffered saline (PBS);

(2) 0.1 ml of phosphate buffered saline; or (3) eye inserts each containing 400 $\mu$g of poly I:C.

The first treatment occurred 6 hours prior to infection and continued once daily for 4 days. Prior to treatment each day, each eye was swabbed to recover infectious virus, and the HSV-1 titer was determined in each case and the results are recorded in Table I.

TABLE I

Rabbit Eye Insert - Experiment 1

| Rabbit Eye Treatment | Animal Treated ID Number | Eye | Herpes Simples Virus Titer on Day[a] 0 (Pre) | 1 | 2 | 3 | 4 |
|---|---|---|---|---|---|---|---|
| Placebo (PBS) | 3 | L | −0.3 | 2.0 | 3.4 | 3.4 | 2.7 |
|  |  | R | −0.3 | 2.0 | 3.9 | 2.9 | 3.4 |
|  | 4 | L | −0.3 | 0.7 | 4.0 | 3.0 | 2.9 |
|  |  | R | −0.3 | −0.3 | 3.0 | 2.4 | 3.4 |
|  | GMT |  | −0.3 | 1.1 | 3.6 | 2.9 | 3.1 |
| Poly I:C in PBS | 1 | L | −0.3 | −0.3 | 2.0 | 1.9 | 1.4 |
|  |  | R | −0.3 | 1.0 | 3.4 | 3.0 | 2.9 |
|  | 2 | L | −0.3 | 1.9 | 2.4 | 2.7 | 3.4 |
|  |  | R | −0.3 | −0.3 | 1.7 | 3.0 | 3.4 |
|  | GMT |  | −0.3 | 0.6 | 2.4 | 2.7 | 2.8 |
| Poly I:C Insert | 5 | L | −0.3 | −0.3 | −0.3 | −0.3 | −0.3 |
|  |  | R | −0.3 | −0.3 | −0.3 | −0.3 | −0.3 |
|  | 6 | L | −0.3 | −0.1 | 3.7 | 4.4 | 3.0 |
|  |  | R | −0.3 | −0.3 | −0.3 | −0.3 | −0.3 |
|  | GMT |  | −0.3 | −0.3 | 0.7 | 0.9 | 0.5 |

GMT = log Geometric Mean Titer

[a] Titers are expressed as $\log_{10}$ of the infectious virus concentration ($TCID_{50}$) determined following exposure of cultures of guinea pig embryo cells to serial 10-fold dilutions of virus samples and incubation at 36° C. for 5 days. −0.3 was assigned to those samples containing no infectious virus.

EXAMPLE 2

A second experiment was conducted substantially as described in Example 1, but employing the following treatment groups of 2 rabbits each:

(1) eye inserts each containing approximately 400 μg of poly I:C;
(2) placebo eye inserts;
(3) 0.1 ml of phosphate buffered saline The HSV-1 titers are shown in Table II.

TABLE II

Rabbit Eye Insert - Experiment 2

| Rabbit Eye Treatment | Animal Treated ID Number | Eye | Herpes Simplex Virus Titer on Day[a] 1 | 2 | 3 | 4 |
|---|---|---|---|---|---|---|
| Placebo (PBS) | 5 | L | 0.0 | 1.7 | 3.4 | 3.7 |
|  |  | R | −0.3 | −0.3 | 1.9 | 3.9 |
|  | 6 | L | −0.3 | −0.3 | 0.4 | 2.7 |
|  |  | R | −0.3 | 0.0 | 2.7 | 3.0 |
|  | GMT |  | −0.2 | 0.3 | 2.1 | 3.3 |
| Insert Placebo | 3 | L | −0.3 | 2.0 | 4.0 | 3.9 |
|  |  | R | −0.3 | 1.4 | 3.9 | 4.0 |
|  | 4 | L | −0.3 | 2.7 | 3.0 | 3.7 |
|  |  | R | 0.0 | 1.0 | 0.9 | 3.0 |
|  | GMT |  | −0.2 | 1.8 | 3.0 | 3.7 |
| Poly I:C Insert | 1 | L | −0.3 | 0.9 | 0.9 | 1.9 |
|  |  | R | −0.3 | 0.7 | −0.3 | −0.3 |
|  | 2 | L | 0.4 | 0.0 | 0.7 | −0.3 |
|  |  | R | −0.3 | 0.7 | 1.0 | 1.7 |
|  | GMT |  | −0.1 | 0.6 | 0.6 | 0.8 |

GMT = log Geometric Mean Titer

[a] Titers are expressed as $\log_{10}$ of the infectious virus concentration ($TCID_{50}$) determined following exposure of cultures of guinea pig embryo cells to serial 10-fold dilutions of virus samples and incubation at 36° C. for 5 days. −0.3 was assigned to those samples containing no infectious virus.

EXAMPLE 3

| Controlled Release Formulation of Poly I:C Adapted For Use As An Eye-Insert | |
|---|---|
| Polyribocytidylic acid potassium salt | 225 mg |
| Polyriboinosinic acid potassium salt | 216 mg |
| Hydroxypropylcellulose (Klucel HF) | 3970 mg |

1. Add polyribocytidylic acid potassium salt to 10 ml of distilled water. Result is a thick gel. "Solution A".

2. Add polyriboinosinic acid potassium salt to 10 ml of distilled water. Result is a thick gel. "Solution B".

3. Store Solution A and Solution B at 5° C. for 16 to 18 hours.

4. Place 100 g of distilled boiling water in 250 ml beaker.

5. Slowly add all of the hydroxypropylcellulose to the hot water.

6. Stir the slurry of hydroxypropylcellulose until a gel forms. Allow the gel to cool to room temperature. "Gel C". Store Gel C at 5° C. for 16 to 18 hours.

7. Combine Solution A, Solution B and Gel C in a small desicating dish. "Gel D".

8. Freeze dry Gel D to a dry cake.

9. Compress the dry cake into a flat sheet which is 1 mm thick.

10. Cut pieces from the 1 mm film which are rectangular in shape and which weight approximately 10 mg each (actual weight approximately 11.5 mg).

11. Store pieces at 5° C. until used.

What is claimed is:

1. An improved method of treating virus infections of skin, eye and mucous membrane tissue susceptible to treatment with interferon by topically applying a therapeutically effective antiviral amount of an interferon inducer selected from the group consisting of synthetic double-stranded RNA, a natural double-stranded RNA, and a nonpolynucleotide, the improvement consisting of incorporating said interferon inducer and a water soluble polymer selected from the group consisting of cellulose ethers, polyvinyl alcohol, polyvinylpyrrolidone, carboxyvinylpolymer and polyethylene glycol.

2. An improved composition for the treatment of virus infections of skin, eye and mucous membrane tissue susceptible to treatment with interferon comprising a therapeutically effective antiviral amount of an interferon inducer selected from the group consisting of synthetic double-stranded RNA, natural double-stranded RNA, and a nonpolynucleotide, the improvement consisting of incorporating said interferon inducer in a homogeneous mixture of said interferon inducer and a water soluble polymer selected from the group consisting of cellulose ethers, polyvinyl alcohol, polyvinylpyrrolidone, carboxyvinylpolymer and polyethylene glycol.

3. The method of claim 1 wherein the interferon inducer is poly I:C.

4. The method of claim 1 or 3 wherein the tissue is that of the eye.

5. The formulation of claim 2 wherein the water-soluble polymer is a cellulose ether.

6. The formulation of claim 2 wherein the cellulose ether is hydroxypropylcellulose.

7. The formulation of claim 2, 5 or 6 wherein the interferon inducer is poly I:C.

8. The formulation of claim 2, 5 or 6 adapted for use on the eye, wherein the interferon inducer is poly I:C.

* * * * *